United States Patent [19]
Goltra

[11] Patent Number: 5,802,495
[45] Date of Patent: Sep. 1, 1998

[54] PHRASING STRUCTURE FOR THE NARRATIVE DISPLAY OF FINDINGS

[76] Inventor: Peter Goltra, 22717 Goltra La., Middleburg, Va. 22117

[21] Appl. No.: 609,835

[22] Filed: Mar. 1, 1996

[51] Int. Cl.$^6$ .......................... G06F 159/00; G06F 17/22
[52] U.S. Cl. ................. 705/3; 704/1; 704/9; 707/534; 707/540; 395/54
[58] Field of Search ................... 395/202, 203, 395/796, 10, 12, 54; 704/9, 10, 1; 705/2, 3; 707/530, 531, 534, 540, 532

[56] References Cited

U.S. PATENT DOCUMENTS

| | | | |
|---|---|---|---|
| 3,566,370 | 2/1971 | Worhington, Jr. et al. | 340/172.5 |
| 4,428,733 | 1/1984 | Kumar-Misir | 434/363 |
| 4,503,426 | 3/1985 | Mikulski | 345/171 |
| 4,839,822 | 6/1989 | Dormond et al. | 600/300 |
| 4,869,531 | 9/1989 | Rees | 283/67 |
| 4,878,175 | 10/1989 | Norden-Paul et al. | 395/202 |
| 5,023,785 | 6/1991 | Adrion et al. | 128/630 |
| 5,089,978 | 2/1992 | Lipner et al. | 364/551.01 |
| 5,262,943 | 11/1993 | Thibado et al. | 600/300 |
| 5,265,010 | 11/1993 | Evans-Paganelli et al. | 128/630 |
| 5,296,688 | 3/1994 | Hamilton et al. | 235/375 |
| 5,305,205 | 4/1994 | Weber et al. | 395/793 |
| 5,327,341 | 7/1994 | Whalen et al. | 395/203 |
| 5,387,164 | 2/1995 | Brown, Jr. | 482/9 |

OTHER PUBLICATIONS

International Search Report dated Apr. 18, 1997.

*Primary Examiner*—David R. Hudspeth
*Assistant Examiner*—Joseph Thomas
*Attorney, Agent, or Firm*—Burns, Doane, Swecker and Mathis, L.L.P.

[57] ABSTRACT

A method for generating sentences of text for selected medical findings in an electronic medical diagnostic system is disclosed. First, a descriptive phrase for each medical finding is created. Each descriptive phrase is then analyzed to determine possible truncation points for modifying the descriptive phrase of one medical finding if another medical finding is also selected. A code at each possible truncation point is then entered into the phrase. Language to be inserted at each of the truncation points is then created and the descriptive phrase and modifying language are stored. Finally, the stored descriptive phrases and modifying language are then combined to form a readable text for the medical findings selected from the database.

8 Claims, 3 Drawing Sheets

HIERARCHIAL LEVELS FOR
MEDICAL FINDING
"HEART SOUNDS"

TOP LEVEL:
~T THE HEART SOUNDS WERE ABNORMAL
~5.1 NORMAL

2ND LEVEL:
THE S1 ~T WAS ABNORMAL
~4.1 NORMAL

3RD LEVEL:
WAS ~L DIMINISHED
~1.0 NOT

FIG. 3

PHRASING STRUCTURE FOR THE NARRATIVE DISPLAY OF FINDINGS

FIELD OF THE INVENTION

The present invention relates to a method and apparatus for producing a readable and coherent narrative from a plurality of findings stored in a hierarchical database.

BACKGROUND OF THE INVENTION

While many aspects of the operation and administration at hospitals and other healthcare facilities have been computerized over the past years, one of the most important aspects, the generation of patient charts, the updating of these charts and the generation of care plans by healthcare professionals such as doctors, nurses, therapists, and the like, is still performed largely by hand. As a result, while a patient chart of some type is normally generated shortly after a patient is admitted to the healthcare facility for a particular service, for example, an intensive care unit, cardiac surgery unit, or the like, the chart may not always be updated to reflect actual progress by the patient.

Even after a diagnosis has been made and a care plan has been devised, the patient chart may not be referred to when the healthcare professional is preparing progress notes on the patient. Thus, there is no check to assure that the original treatments have in fact been followed, or that proposed resolution dates in the chart have been met or updated. When changes in the chart are made as a result of changes in the status of a patient, such changes are frequently not entered in the original chart. Thus, good archival records are not generally maintained for changes in treatment. The professional notes for a particular patient frequently do not include an updated version of the patient's chart. Further, even though a form may be available for progress notes, the form does not take into account the unique problems of the individual patient, and does not give the healthcare professional a checklist of items to be investigated for such problems or suggested interventions or resolution dates for the particular patient problem. When changes are made or expected outcomes are not achieved, the reasons for such occurrences are seldom provided, making any further review far more difficult. Again, a good archival record of what has been done for the particular patient is not readily available. Because of the absence of good archival records, and the absence of reasons for changes or deviations, tracking a problem for quality control, legal or other reasons is difficult, and it is difficult to research the relative effectiveness of various interventions or to perform other research from the records.

The lack of a complete archival record can also cause significant problems for healthcare professionals who must adequately document the examination and treatment of patients whose medical bills are being paid by insurance companies. If the healthcare professional does not provide proper documentation, the insurance companies will not pay the bills. Furthermore, healthcare professionals have less time to spend with each patient these days. As a result, the healthcare professional does not have time to figure out from the original chart and the added progress notes, if they are available, the previous problems of the patient and what treatments were prescribed. Thus, the healthcare professional needs to have an easy way to review charts for each patient.

Even with dictated, free text-based computer patient chart and/or progress note systems, many of the problems indicated above still exist. Such systems also in many instances lack flexibility so as to be configurable by the healthcare professional so as to provide specific help in locating or entering information and for prompting the healthcare professional with lists of symptoms, questions which should be asked and tests that should be performed in certain circumstances. In addition, they frequently do not give the healthcare professional the ability to add special instructions or to add items as required. Further, it is generally not possible to obtain either an updated chart or historical chart upon request. Thus, there is a need for a computer medical system based on coded medical findings in a logical hierarchical database structure which enhances the diagnostic capabilities of a healthcare provider, provides structured patient charts as well as formatted updated or historical care plans.

However, the problem with hierarchical database structures is the display of the medical findings. An indented outline format wastes space. However, due to the hierarchical structure of the medical findings where there are many subsets and subsets of subsets for each medical finding, a straightforward linking of phrases would produce a narrative which is difficult to read. In addition, creating the negative of a phrase can produce gibberish. For example, a subset of trauma includes head, chest, abdomen, etc. A person subjected to chest trauma but not to head trauma would generate the sentence: trauma chest no head. Thus, there is a need for a phrasing structure for producing a coherent narrative display of medical findings.

SUMMARY OF THE INVENTION

It is an object of the present invention to overcome the problems cited above by providing a method and apparatus for producing coherent phrasing structure for a narrative based on selected informational findings stored in a hierarchical database.

According to one embodiment of the present invention, a method for generating sentences of text for selected medical findings in an electronic medical diagnostic system is disclosed. First, a descriptive phrase for each medical finding is created. Each descriptive phrase is then analyzed to determine possible truncation points for modifying the descriptive phrase of one medical finding if another medical finding is also selected. A code at each possible truncation point is then entered into the phrase. Language to be inserted at each of the truncation points is then created and the descriptive phrase and modifying language are stored. Finally, the stored descriptive phrases and modifying language are then combined to form a readable text for the medical findings selected from the database.

BRIEF DESCRIPTION OF THE DRAWINGS

These and other features and advantages of the present invention will be readily apparent to one of ordinary skill in the art from the following written description, used in conjunction with the drawings, in which:

FIG. 3 illustrates an example of a stored hierarchical structure for a medical finding according to one embodiment of the present invention.

DETAILED DESCRIPTION

Figure 1:
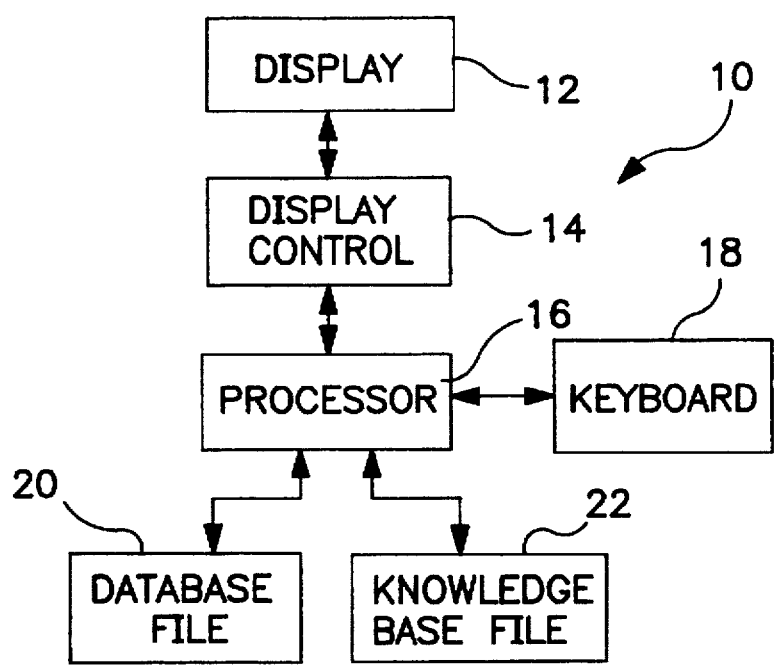
FIG. 1 illustrates a block diagram of a computer based medical system according to one embodiment of the present invention.

The present invention can be applied to any situation where a narrative needs to be created for a plurality of findings which are stored in a coded hierarchical database. It will be apparent to one skilled in the art that many fields such as medicine, law, engineering, etc. use hierarchical databases and that the present invention can be used in all of these fields. The present invention will be explained using a computer based medical system with a hierarchical medical findings database or an example. It will be understood that the present invention is not limited thereto. A block diagram of the computer based medical system suitable for use in practicing the teachings of the present invention is illustrated in FIG. 1. The medical system 10 contains a processor 16 with one or more input devices such as a keyboard 18. The processor 16 also has a database file or memory 20 and a knowledge base file or memory 22. The processor 16 operates a standard display controller 14 which in turn controls a display device 12 at the workstation. The display device 12 can be any standard type of display monitor, attached or wireless. Furthermore, the apparatus 10 can be networked to other such medical systems not illustrated which can be placed around the hospital or healthcare facility. This allows multiple people to use the healthcare system for the same or for multiple patients.

The present invention is based upon medical findings. Medical findings are defined as symptoms, history, physical findings, diagnoses, tests, and therapy which may be present for a particular patient. The database file 20 contains over 50,000 medical findings and is divided into categories such as symptoms, history, physical findings, diagnoses, tests, and therapy. Furthermore, the descriptions of the medical findings stored in the database memory 20 are hierarchical and can have up to 8 levels of description. The first level gives the simplest explanation of a medical finding, for example, a cough. The explanations become more detailed the lower the level. As noted above, a first level finding may be a cough while a second level finding may be a brassy cough. Another feature of the database file 20 is that all of the medical findings are coded so as to be distinct from each other. For example, each medical finding can be assigned an internal number which uniquely identifies that particular medical finding. In addition, each medical finding also contains a code which indicates which category within the database file 20 the medical finding is associated with. For example, a medical finding may contain the code SYM to indicate that the medical finding is associated with the symptom section; HIS to indicate that the medical finding is associated with the history section; PHY to indicate that the medical finding is associated with the physical section; DIS to indicate that the medical finding is associated with the diagnoses section; TST to indicate that the medical finding is associated with the test section; and RX to indicate that the medical finding is associated with the therapy section.

As noted above, the medical system 10 also contains a knowledge base file 22. The knowledge base file 22 contains a detailed description of over 2000 diagnoses. The detailed description of the diagnoses uses the medical finding terms which are stored in the database file 20. For each diagnosis, each medical finding associated with the diagnosis is assigned a numerical value depending on how important such a medical finding may be to the diagnosis. For example, in the detailed description of the diagnosis for coronary artery stenosis, medical findings such as chest pain or discomfort and dyspnea (shortness of breath), which are a strong showing of coronary artery stenosis, will be given high values while a lack of an appetite may not be described in the diagnosis at all or given a very low value. For example, the medical findings can be assigned values between 0 and 20 wherein the value 20 is the highest value that can be given to an important medical finding, however, the invention is not limited thereto. Thus, the values assigned to each medical finding within the detailed description is proportional to how important such a medical finding is to the diagnosis. Furthermore, the values can vary for a given medical finding depending on a plurality of factors such as age of the patient and timeframe, i.e., when a symptom occurred in relation to other symptoms. For example, a white blood cell count of 18,000 may be given a high value if the patient is an adult while the same medical finding is not given a value at all if the patient is a new-born child because this is normal for a new-born child.

Here again, the medical findings used in the detailed description of the diagnosis are all coded. In addition, over 400,000 links are provided between the database file 20 and the knowledge base file 22. In other words, the findings in the database file 20 occur over 400,000 times in the knowledge base file 22.

The detailed description of the diagnoses stored in the knowledge base file 22 contain lists of symptoms as well as personal and family history and physical findings that a patient should or may have experienced. In addition, the detailed diagnoses contain lists of tests, possible therapies, and medications which might be prescribed for the patient if the healthcare professional decides that the patient is experiencing a particular illness or problem.

A patient chart is created by selecting various medical findings in the database file 20 which are being displayed by a clinical protocol or a template on the display screen 18. Clinical protocols are a structured combination of coded medical phrases selected from the database file 20 which are related or associated with a particular disease or problem. The creation of patient charts is explained in more detail in U.S. patent application Ser. No. 08/609,828, entitled "Creating and Using Protocols to Create a Patient Chart," which is being filed concurrently herewith, and presently pending, and is expressly incorporated herein by reference.

When it is necessary to generate a patient's chart, the present invention provides a phrasing structure so that a medical chart or care plan created using a medical system 10 can be produced on paper or on the display screen with a coherent text. In other words, rather than simply printing out a chart or care plan with a plurality of indented medical findings entered into the various sections of the chart or care plan, the present invention provides a method for changing the entered medical findings into a coherent narrative with sentence and paragraph structure. The phrasing structure according to the present invention includes controls for determining how much of a phrase should be used, where values need to be inserted, and what term or alternate phrase is to be used when the negative of the medical finding is selected.

Figure 2:
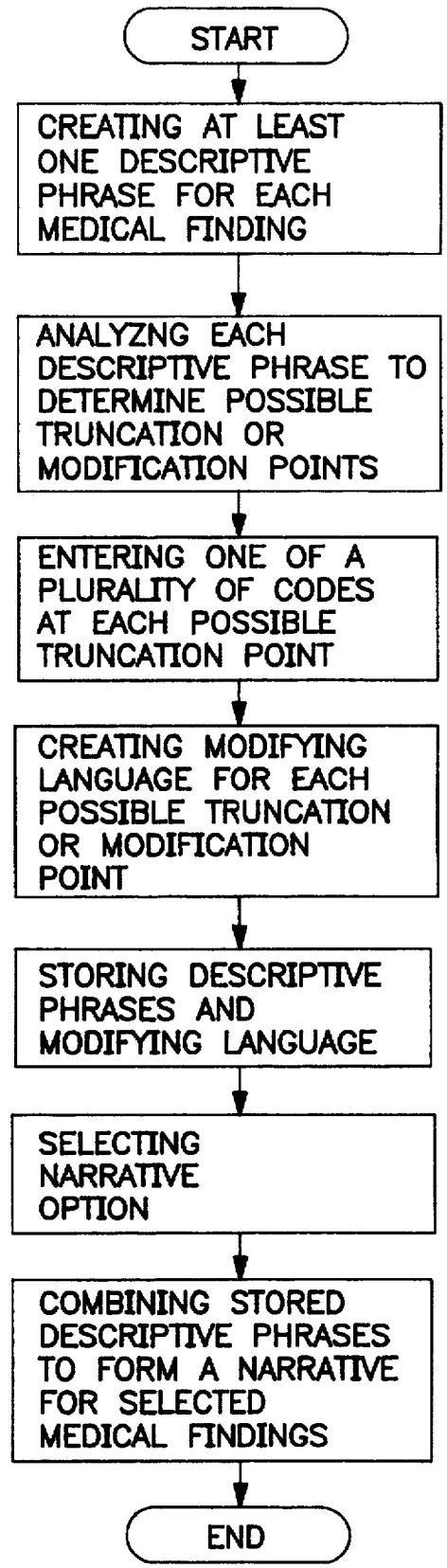
FIG. 2 illustrates a flowchart describing the operation of one embodiment of the present invention.

The phrasing structure of the present invention will now be described in more detail with reference to the flowchart illustrated in FIG. 2. As noted above, medical findings and other terms are stored in the database 20. For each medical finding, a descriptive phrase is written for each term. If there are to be subsidiary terms, the phrase is analyzed to see where to break the phrase for the combination of the phrase and the subsidiary phrases to read correctly. This is performed by entering one of a plurality of codes at the designated mandatory or conditional truncation point. These descriptive phrases are then stored in a location identified by the internal number code of the medical finding for which the descriptive phrase has been generated.

In one embodiment of the present invention, a plurality of codes are provided to shorten a phrase, make a phrase negative, insert a value into the phrase, change the status of the phrase or a term within the phrase, indicate a test result level, modify the phrase by adding an adjective or adverb, or for deleting and adding terms to the phrase. For example, the code "~T" can be used to indicate a possible truncation point within a phrase. The code "~C" can be used to indicate a conditional shortening of the phrase. The code "~V" is used to indicate a place within the phrase were a value can be inserted. The codes "~L" and "~M" indicate places within the phrase where adverbs or adjectives, respectively, can be added. The code "~S" is used to indicate the status, i.e., history, family history, etc., of a term in the phrase. The code "~R" is used to modify a phrase to indicate whether test results were high, low, abnormal, etc. Finally, the code "~#.# (phrase or word)" can be used to modify a positive phrase, wherein the first number in the code indicates the number of words to skip in the positive phrase, the second number indicates the number of words which are deleted and the word or phrase following the second number in the code are inserted into the positive phrase in place of the deleted words. It will be understood that these specific codes are given only as an example of possible codes which could be used in the present invention and the present invention is not limited thereto.

For each hierarchical level of a medical finding, a positive phrase and possibly a negative version of the positive phrase are stored. In this example, the negative version always operates on the positive phrase by either deleting and replacing some words in the phrase or by replacing the entire phrase. Likewise, the positive and negative descriptive phrases at lower levels of the hierarchy operate on the higher level phrases as will be illustrated below in the discussion concerning FIG. 3. It will be understood however, that equivalent files may exist in such a way to allow a sentence to be started or formed for a medical finding no matter what hierarchical level is accessed.

When a medical finding is selected to be included in a patient chart, the medical finding is stored with a plurality of codes. For example, the internal number code which identifies the medical finding is stored with the medical finding along with a code which indicates whether positive or negative has been selected for the medical finding. Thus, when the narrative is produced, the system knows whether to use the positive phrase or the negative modification for each medical finding by looking at the codes.

According to one embodiment of the present invention, the healthcare professional can select different formats in which the narrative is produced. For example, a technical format can be selected wherein the narrative is produced using technical or medical phrases that will be understood by a healthcare professional but maybe not understood by a lay person. If the narrative is going to be read by a lay person, the healthcare professional can select the non-technical format which produces a narrative in plain and simple to understand terms. Furthermore, either the technical or non-technical format can be selected and be reproduced in a variety of different languages, for example, English, Spanish, French, German, etc. This is accomplished by creating technical and non-technical phrases and sentences for each medical finding in each language desired. Each of the phrases is then stored along with a code which tells the system that the phrase is technical or non-technical as well as a code for indicating the language of that particular phrase. Thus, when the healthcare professional selects the non-technical format in Spanish off of the display screen, the system creates a narrative for all of the selected medical findings using the stored phrases and sentences with the codes that indicate the non-technical format and the selection of the Spanish language.

FIG. 3 illustrates an example of code usage to create readable phrases for medical findings. In this example, the medical finding is for heart sounds. The medical finding for heart sounds has a plus sign displayed next to it. The plus sign indicates that there are several levels of responses for the general medical finding of heart sounds. The first level states that "the heart sounds were abnormal." The second level states that "the S1 was abnormal." Finally, the third level states that "the S1 was mildly diminished." Along with each positive recitation of the medical finding is also a coded negative phrase. Thus, if the healthcare professional selects the positive response by pointing at the first three letters in the phrase "heart sounds," the phrase reads as is, i.e., "the heart sounds were abnormal." However, if the healthcare professional selects the negative response for the top level, the system looks at the coded message "~5.1 normal" and counts out 5 words as indicated by the 5 and deletes one word as indicated by the 1, thus deleting the word "abnormal" and adds to the sentence "normal." Thus, the sentence would read: "The heart sounds were normal." If the healthcare professional decides to use the second level description, and the positive message is selected, the system looks at the coded message "The S1~T was abnormal." The coded value "~T" removes all of the level 1 message and adds the layer 2 phrase. Thus, the phrase will read: "The S1 was abnormal." Here again, if the negative of the second level is selected, the system looks at the coded message "~4.1 normal" and counts out 4 words and removes 1 word, thus removing "abnormal" and inserting "normal" into the sentence. The sentence would thus read: "The S1 was normal."

If the healthcare professional uses the level 3 description for heart sounds, the level 2 message is truncated after "S1" and the layer 3 message is added. In this example, there is a code "~L" which indicates that a modifier may be added if selected by the healthcare professional, for example, mildly. In this case, the sentence will read: "The S1 was mildly diminished." However, if the negative response for the layer 3 description is selected and no modifier was selected, the system counts out 1 word and adds "not" and then removes the code "~L." The result would read: "The S1 was not diminished." In all cases, the phrases are printed without the codes.

The principles, preferred embodiments and the modes of operation of the present operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes, and equivalents which fall within the spirit and scope of the present invention as defined in the claims be embraced thereby.

What is claimed is:

1. A method for generating sentences of text, for selected medical finding in an electronic medical diagnostic system, comprising the steps of:

creating a descriptive phrase for each finding;

analyzing each descriptive phrase to determine possible truncation points for modifying the descriptive phrase of one medical finding if another medical finding is also selected;

entering a code at each possible truncation point;

creating language to be inserted at each coded truncation point;

storing said descriptive phrases and modifying language in a hierarchical database wherein lower layered modifying language modifies higher layered phrases; and combining stored descriptive phrases and modifying language to form written text from said selected medical findings according to the codes entered into each descriptive phrase.

2. A method according to claim 1, wherein said descriptive phrases are complete sentences.

3. A method according to claim 1, wherein said modifying language is used to create the negative form of the descriptive phrase.

4. A method according to claim 1, further comprising the step of:

placing codes in said descriptive phrases wherein numerical values need to be entered into the phrase.

5. A method according to claim 1, wherein hierarchical level numbers can be assigned to each descriptive phrase to determine whether the selected phrase should start a new sentence or paragraph.

6. A method according to claim 1, wherein said medical findings are stored in a database, wherein the database contains a symptoms section, a history section, a physical findings section, a diagnosis section, a test section, and a therapy section.

7. A method according to claim 6, wherein a narrative for selected medical findings in each section of the database can be generated.

8. A method according to claim 1, wherein a number is stored with each descriptive phrase so as to allow substitution of an equivalent descriptive phrase in a different language when requested.

* * * * *